(12) United States Patent
Hegg et al.

(10) Patent No.: US 7,833,264 B2
(45) Date of Patent: Nov. 16, 2010

(54) BIFURCATED STENT

(75) Inventors: Jens Hegg, Minneapolis, MN (US);
Michael P. Meyer, Richfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 254 days.

(21) Appl. No.: 11/368,769

(22) Filed: Mar. 6, 2006

(65) Prior Publication Data

US 2007/0208418 A1    Sep. 6, 2007

(51) Int. Cl.
*A61F 2/06* (2006.01)
(52) U.S. Cl. .................................. 623/1.35; 623/1.15
(58) Field of Classification Search ............. 623/1.15, 623/1.27, 1.44, 1.35, 1.16, 1.11
See application file for complete search history.

(56) References Cited

U.S. PATENT DOCUMENTS

| | | | |
|---|---|---|---|
| 4,309,994 A | 1/1982 | Grunwald | 128/214 R |
| 4,769,005 A | 9/1988 | Ginsburg et al. | 604/53 |
| 4,774,949 A | 10/1988 | Fogarty | 128/348.1 |
| 4,896,670 A | 1/1990 | Crittenden | 606/194 |
| 4,905,667 A | 3/1990 | Foerster et al. | 128/4 |
| 4,994,071 A | 2/1991 | MacGregor | 606/194 |
| 5,342,387 A | 8/1994 | Summers | 606/198 |
| 5,387,235 A | 2/1995 | Chuter | 623/1 |
| 5,456,712 A | 10/1995 | Maginot | 623/1 |
| 5,476,471 A | 12/1995 | Shifrin et al. | 606/151 |
| 5,487,730 A | 1/1996 | Marcadis et al. | 604/96 |
| 5,591,228 A | 1/1997 | Edoga | 623/1 |
| 5,607,444 A | 3/1997 | Lam | 606/194 |
| 5,609,605 A | 3/1997 | Marshall et al. | 606/191 |
| 5,609,627 A | 3/1997 | Goicoechea et al. | 623/1 |
| 5,613,980 A | 3/1997 | Chauhan | 606/194 |
| 5,617,878 A | 4/1997 | Taheri | 128/898 |
| 5,632,762 A | 5/1997 | Myler | 606/194 |

(Continued)

FOREIGN PATENT DOCUMENTS

CA    2220864    7/1999

(Continued)

OTHER PUBLICATIONS

U.S. Appl. No. 09/325,996, filed Jun. 4, 1999, Vardi et al.

(Continued)

*Primary Examiner*—Todd E Manahan
*Assistant Examiner*—Erin Colello
(74) *Attorney, Agent, or Firm*—Vidas Arrett & Steinkraus

(57) ABSTRACT

A stent, with expanded and unexpanded configurations, comprises a substantially tubular body having a proximal end region, a distal end region, and defining a first lumen therethrough. The tubular body comprises a plurality of adjacent deployable elements positioned between the proximal end region and distal end region. In the expanded configuration the deployable elements define a second lumen. The first lumen has a first longitudinal axis and the second lumen has a second longitudinal axis which is at an oblique angle relative to the first longitudinal axis. The first lumen is in fluid communication with the second lumen. The tubular body comprises a track region which further comprises at least two struts. The struts are substantially parallel to each other and the first longitudinal axis in the unexpanded configuration. The track region is comprised of at least one of the deployable elements.

15 Claims, 5 Drawing Sheets

U.S. PATENT DOCUMENTS

| | | | |
|---|---|---|---|
| 5,632,763 A | 5/1997 | Glastra | 606/194 |
| 5,632,772 A | 5/1997 | Alcime et al. | 623/1 |
| 5,636,641 A | 6/1997 | Fariabi | 600/585 |
| 5,669,924 A | 9/1997 | Shaknovich | 606/108 |
| 5,669,932 A | 9/1997 | Fischell et al. | 606/198 |
| 5,676,697 A | 10/1997 | McDonald | 623/1 |
| 5,683,450 A | 11/1997 | Goicoechea et al. | 623/1 |
| 5,697,971 A | 12/1997 | Fischell et al. | 623/1 |
| 5,707,348 A | 1/1998 | Krogh | 602/41 |
| 5,709,713 A | 1/1998 | Evans et al. | 623/1 |
| 5,720,735 A | 2/1998 | Dorros | 604/284 |
| 5,749,825 A | 5/1998 | Fischell et al. | 600/3 |
| 5,749,890 A | 5/1998 | Shaknovich | 606/198 |
| 5,755,734 A | 5/1998 | Richter et al. | 606/194 |
| 5,755,735 A | 5/1998 | Richter et al. | 606/194 |
| 5,755,771 A | 5/1998 | Penn et al. | 623/1 |
| 5,755,773 A | 5/1998 | Evans et al. | 623/1 |
| 5,755,778 A | 5/1998 | Kleshinski | 623/1 |
| 5,782,906 A | 7/1998 | Marshall et al. | 623/1 |
| 5,824,036 A | 10/1998 | Lauterjung | 623/1 |
| 5,824,040 A | 10/1998 | Cox et al. | 623/1 |
| 5,827,320 A | 10/1998 | Richter et al. | 606/194 |
| 5,851,464 A | 12/1998 | Davila et al. | 264/103 |
| 5,868,777 A | 2/1999 | Lam | 606/194 |
| 5,893,887 A | 4/1999 | Jayaraman | 623/1 |
| 5,906,640 A | 5/1999 | Penn et al. | 623/1 |
| 5,961,548 A | 10/1999 | Shmulewitz | 623/1 |
| 5,972,017 A | 10/1999 | Berg et al. | 606/198 |
| 6,013,054 A | 1/2000 | Jiun Yan | 604/96 |
| 6,013,091 A | 1/2000 | Ley et al. | 606/191 |
| 6,017,324 A | 1/2000 | Tu et al. | 604/96 |
| 6,017,363 A | 1/2000 | Hojeibane | 623/1 |
| 6,030,414 A | 2/2000 | Taheri | 623/1 |
| 6,033,433 A | 3/2000 | Ehr et al. | 623/1 |
| 6,033,434 A | 3/2000 | Borghi | 623/1 |
| 6,033,435 A | 3/2000 | Penn et al. | 623/1 |
| 6,048,361 A | 4/2000 | Von Oepen | 623/1 |
| 6,056,775 A | 5/2000 | Borghi et al. | 623/1.16 |
| 6,059,824 A | 5/2000 | Taheri | 623/1 |
| 6,068,655 A | 5/2000 | Seguin et al. | 623/1 |
| 6,086,611 A | 7/2000 | Duffy et al. | 623/1 |
| 6,093,203 A | 7/2000 | Uflacker | 612/1.12 |
| 6,096,073 A | 8/2000 | Webster et al. | 623/1.16 |
| 6,099,497 A | 8/2000 | Adams et al. | 604/96.01 |
| 6,113,579 A | 9/2000 | Eidenschink et al. | 604/264 |
| 6,117,117 A | 9/2000 | Mauch | 604/284 |
| 6,117,156 A | 9/2000 | Richter et al. | 606/194 |
| 6,129,738 A | 10/2000 | Lashinski et al. | 606/194 |
| 6,129,754 A | 10/2000 | Kanesaka et al. | 623/1 |
| 6,142,973 A | 11/2000 | Carleton et al. | 604/96 |
| 6,143,002 A | 11/2000 | Vietmeier | 606/108 |
| 6,159,238 A | 12/2000 | Killion et al. | 612/1.11 |
| 6,165,195 A | 12/2000 | Wilson et al. | 606/194 |
| 6,168,621 B1 | 1/2001 | Vrba | 623/1.2 |
| 6,183,509 B1 | 2/2001 | Dibie | 623/1.35 |
| 6,203,568 B1 | 3/2001 | Lombardi et al. | 623/1.13 |
| 6,210,380 B1 | 4/2001 | Mauch | 604/284 |
| 6,210,429 B1 * | 4/2001 | Vardi et al. | 623/1.11 |
| 6,210,433 B1 | 4/2001 | Larre | 623/1.15 |
| 6,254,593 B1 | 7/2001 | Wilson | 606/1.11 |
| 6,258,115 B1 | 7/2001 | Dubrul | 606/200 |
| 6,258,116 B1 | 7/2001 | Hojeibane | 623/1.16 |
| 6,261,305 B1 | 7/2001 | Marotta et al. | 606/200 |
| 6,261,316 B1 | 7/2001 | Shaolian et al. | 623/1.11 |
| 6,264,662 B1 | 7/2001 | Lauterjung | 606/108 |
| 6,264,686 B1 | 7/2001 | Rieu et al. | 623/1.16 |
| 6,290,673 B1 | 9/2001 | Shanley | 604/102.02 |
| 6,293,968 B1 | 9/2001 | Taheri | 623/1.15 |
| 6,325,826 B1 | 12/2001 | Vardi et al. | 623/1.35 |
| 6,334,864 B1 | 1/2002 | Amplatz et al. | 606/200 |
| 6,334,870 B1 | 1/2002 | Ehr et al. | 623/1.16 |
| 6,346,089 B1 | 2/2002 | Dibie | 603/1.15 |
| 6,355,060 B1 | 3/2002 | Lenker et al. | 623/1.34 |
| 6,361,544 B1 | 3/2002 | Wilson et al. | 606/194 |
| 6,361,555 B1 | 3/2002 | Wilson | 623/1.11 |
| 6,383,213 B2 | 5/2002 | Wilson et al. | 623/1.11 |
| 6,395,018 B1 | 5/2002 | Castaneda | 623/1.13 |
| 6,436,104 B2 | 8/2002 | Hojeibane | 606/108 |
| 6,436,134 B2 | 8/2002 | Richter et al. | 623/1.15 |
| 6,488,702 B1 * | 12/2002 | Besselink | 623/1.15 |
| 6,508,836 B2 | 1/2003 | Wilson et al. | 623/1.35 |
| 6,517,558 B2 | 2/2003 | Gittings et al. | 606/153 |
| 6,520,988 B1 | 2/2003 | Colombo et al. | 623/1.35 |
| 6,540,779 B2 | 4/2003 | Richter et al. | 623/1.35 |
| 6,579,309 B1 | 6/2003 | Loos et al. | 623/1.16 |
| 6,579,312 B2 | 6/2003 | Wilson et al. | 623/1.35 |
| 6,582,394 B1 | 6/2003 | Reiss et al. | 604/96.01 |
| 6,596,020 B2 * | 7/2003 | Vardi et al. | 623/1.11 |
| 6,599,316 B2 | 7/2003 | Vardi et al. | 623/1.15 |
| 6,645,242 B1 * | 11/2003 | Quinn | 623/1.16 |
| 6,689,156 B1 | 2/2004 | Davidson et al. | 623/1.11 |
| 6,692,483 B2 | 2/2004 | Vardi et al. | 604/529 |
| 6,695,877 B2 | 2/2004 | Brucker et al. | 623/1.16 |
| 6,706,062 B2 | 3/2004 | Vardi et al. | 623/1.15 |
| 6,749,628 B1 | 6/2004 | Callol et al. | 623/1.15 |
| 6,776,793 B2 | 8/2004 | Brown et al. | 623/1.15 |
| 6,811,566 B1 | 11/2004 | Penn et al. | 623/1.15 |
| 6,835,203 B1 | 12/2004 | Vardi et al. | 623/1.34 |
| 6,858,038 B2 | 2/2005 | Heuser | 623/1.35 |
| 6,884,258 B2 | 4/2005 | Vardi et al. | 623/1.11 |
| 6,896,699 B2 | 5/2005 | Wilson et al. | 623/1.35 |
| 6,932,837 B2 | 8/2005 | Amplatz et al. | 623/1.15 |
| 6,955,687 B2 | 10/2005 | Richter et al. | 623/1.35 |
| 6,955,688 B2 | 10/2005 | Wilson et al. | 623/1.35 |
| 6,962,602 B2 | 11/2005 | Vardi et al. | 623/1.11 |
| 7,018,400 B2 | 3/2006 | Lashinski et al. | 623/1.11 |
| 7,056,323 B2 * | 6/2006 | Mareiro et al. | 606/108 |
| 7,060,091 B2 | 6/2006 | Killion et al. | 623/1.15 |
| 2001/0003161 A1 | 6/2001 | Vardi et al. | 623/1.11 |
| 2001/0004706 A1 | 6/2001 | Hojeibane | 623/1.11 |
| 2001/0004707 A1 | 6/2001 | Dereurne et al. | 623/1.16 |
| 2001/0012927 A1 | 8/2001 | Mauch | 604/284 |
| 2001/0016766 A1 | 8/2001 | Vardi et al. | 623/1.11 |
| 2001/0016767 A1 | 8/2001 | Wilson et al. | 623/1.11 |
| 2001/0016768 A1 | 8/2001 | Wilson et al. | 623/1.11 |
| 2001/0025195 A1 | 9/2001 | Shaolian et al. | 623/1.13 |
| 2001/0027291 A1 | 10/2001 | Shanley | 604/104 |
| 2001/0027338 A1 | 10/2001 | Greenberg | 623/1.13 |
| 2001/0029396 A1 | 10/2001 | Wilson et al. | 623/1.11 |
| 2001/0037116 A1 | 11/2001 | Wilson et al. | 606/108 |
| 2001/0037138 A1 | 11/2001 | Wilson et al. | 623/1.11 |
| 2001/0039448 A1 | 11/2001 | Dibie | 623/1.16 |
| 2001/0049552 A1 | 12/2001 | Richter et al. | 623/1.15 |
| 2001/0056297 A1 | 12/2001 | Hojeibane | 623/1.16 |
| 2002/0013618 A1 | 1/2002 | Marotta et al. | 623/1.15 |
| 2002/0013619 A1 | 1/2002 | Shanley | 623/1.15 |
| 2002/0022874 A1 | 2/2002 | Wilson | 623/1.11 |
| 2002/0026232 A1 | 2/2002 | Marotta et al. | 623/1.16 |
| 2002/0035392 A1 | 3/2002 | Wilson | 623/1.11 |
| 2002/0042650 A1 * | 4/2002 | Vardi et al. | 623/1.35 |
| 2002/0052648 A1 | 5/2002 | McGuckin, Jr. et al. | 623/1.35 |
| 2002/0072790 A1 | 6/2002 | McGuckin, Jr. et al. | 623/1.12 |
| 2002/0111675 A1 | 8/2002 | Wilson | 623/1.35 |
| 2002/0156516 A1 | 10/2002 | Vardi et al. | 623/1.11 |
| 2002/0156517 A1 | 10/2002 | Perouse | 623/1.11 |
| 2002/0165604 A1 | 11/2002 | Shanley | 623/1.15 |
| 2002/0173835 A1 | 11/2002 | Bourang et al. | 623/1.11 |
| 2002/0173840 A1 | 11/2002 | Brucker et al. | 623/1.16 |
| 2002/0183763 A1 | 12/2002 | Callol et al. | 606/108 |
| 2002/0193872 A1 | 12/2002 | Trout, III et al. | 623/1.34 |
| 2002/0193873 A1 | 12/2002 | Brucker et al. | 623/1.35 |
| 2003/0009209 A1 | 1/2003 | Hojeibane | 623/1.11 |
| 2003/0028233 A1 | 2/2003 | Vardi et al. | 623/1.11 |
| 2003/0050688 A1 | 3/2003 | Fischell et al. | 623/1.15 |

| | | | | | |
|---|---|---|---|---|---|
| 2003/0055378 A1 | 3/2003 | Wang et al. .......... 604/103.07 | EP | 1190685 | 3/2002 |
| 2003/0055483 A1 | 3/2003 | Gumm ................... 623/1.11 | EP | 0897700 | 7/2002 |
| 2003/0074047 A1 | 4/2003 | Richter ................. 623/1.11 | EP | 0684022 | 2/2004 |
| 2003/0093109 A1 | 5/2003 | Mauch .................. 606/194 | EP | 1157674 | 7/2005 |
| 2003/0097169 A1 | 5/2003 | Brucker ................ 623/1.11 | EP | 1031330 | 11/2005 |
| 2003/0114912 A1 | 6/2003 | Sequin et al. .......... 623/1.11 | EP | 1070513 | 6/2006 |
| 2003/0125791 A1 | 7/2003 | Sequin et al. .......... 623/1.11 | FR | 2678508 | 1/1993 |
| 2003/0125802 A1 | 7/2003 | Callol et al. ........... 623/1.35 | FR | 2740346 | 10/1995 |
| 2003/0135259 A1 | 7/2003 | Simso ................... 623/1.12 | FR | 2756173 | 11/1996 |
| 2003/0181923 A1 | 9/2003 | Vardi .................... 606/108 | GB | 2337002 | 5/1998 |
| 2003/0195606 A1 | 10/2003 | Davidson et al. ....... 623/1.11 | WO | 88/06026 | 8/1988 |
| 2004/0006381 A1 | 1/2004 | Sequin et al. .......... 623/1.12 | WO | 95/21592 | 8/1995 |
| 2004/0015227 A1 | 1/2004 | Vardi et al. ............ 623/1.16 | WO | 96/29955 | 10/1996 |
| 2004/0044396 A1 | 3/2004 | Clerc et al. ............ 623/1.13 | WO | 96/34580 | 11/1996 |
| 2004/0059406 A1 | 3/2004 | Cully et al. ............ 623/1.11 | WO | 96/41592 | 12/1996 |
| 2004/0088007 A1* | 5/2004 | Eidenschink ............. 607/1 | WO | 97/07752 | 3/1997 |
| 2004/0117003 A1 | 6/2004 | Ouriel et al. .......... 623/1.35 | WO | 97/15346 | 5/1997 |
| 2004/0133268 A1 | 7/2004 | Davidson et al. ....... 623/1.35 | WO | 97/16217 | 5/1997 |
| 2004/0138732 A1 | 7/2004 | Suhr et al. ............. 623/1.11 | WO | 97/26936 | 7/1997 |
| 2004/0138737 A1 | 7/2004 | Davidson et al. ....... 623/1.35 | WO | 97/41803 | 11/1997 |
| 2004/0148006 A1 | 7/2004 | Davidson et al. ....... 623/1.11 | WO | 97/45073 | 12/1997 |
| 2004/0172121 A1 | 9/2004 | Eidenschink et al. ... 623/1.11 | WO | 97/46174 | 12/1997 |
| 2004/0186560 A1 | 9/2004 | Alt ....................... 623/1.35 | WO | 98/19628 | 5/1998 |
| 2004/0225345 A1 | 11/2004 | Fischell et al. ......... 623/1.11 | WO | 98/36709 | 8/1998 |
| 2004/0267352 A1* | 12/2004 | Davidson et al. ....... 623/1.15 | WO | 98/37833 | 9/1998 |
| 2005/0004656 A1 | 1/2005 | Das ...................... 623/1.16 | WO | 98/47447 | 10/1998 |
| 2005/0010278 A1 | 1/2005 | Vardi et al. ............ 623/1.15 | WO | 98/48879 | 11/1998 |
| 2005/0015108 A1 | 1/2005 | Williams et al. ........ 606/194 | WO | 99/03426 | 1/1999 |
| 2005/0015135 A1 | 1/2005 | Shanley ................. 623/1.11 | WO | 99/04726 | 2/1999 |
| 2005/0060027 A1* | 3/2005 | Khenansho et al. ..... 623/1.35 | WO | 99/15103 | 4/1999 |
| 2005/0096726 A1 | 5/2005 | Sequin et al. .......... 623/1.12 | WO | 99/15109 | 4/1999 |
| 2005/0102021 A1 | 5/2005 | Osborne ................ 623/1.13 | WO | 99/24104 | 5/1999 |
| 2005/0102023 A1* | 5/2005 | Yadin et al. ............ 623/1.15 | WO | 99/34749 | 7/1999 |
| 2005/0119731 A1 | 6/2005 | Brucker et al. ......... 623/1.35 | WO | 99/36002 | 7/1999 |
| 2005/0125076 A1 | 6/2005 | Ginn .................... 623/23.65 | WO | 99/36015 | 7/1999 |
| 2005/0131526 A1 | 6/2005 | Wong .................... 623/1.15 | WO | 99/44539 | 9/1999 |
| 2005/0149161 A1 | 7/2005 | Eidenschink et al. ... 623/1.11 | WO | 99/56661 | 11/1999 |
| 2005/0154442 A1 | 7/2005 | Eidenschink et al. ... 623/1.11 | WO | 99/65419 | 12/1999 |
| 2005/0154444 A1 | 7/2005 | Quadri .................. 623/1.13 | WO | 00/07523 | 2/2000 |
| 2005/0183259 A1 | 8/2005 | Eidenschink et al. ...... 29/508 | WO | 00/10489 | 3/2000 |
| 2005/0209673 A1 | 9/2005 | Shaked .................. 623/1.11 | WO | 00/16719 | 3/2000 |
| 2005/0228483 A1 | 10/2005 | Kaplan et al. .......... 623/1.15 | WO | 00/27307 | 5/2000 |
| 2006/0036315 A1* | 2/2006 | Yadin et al. ............ 623/1.35 | WO | 00/27463 | 5/2000 |
| 2006/0041303 A1 | 2/2006 | Israel .................... 623/1.11 | WO | 00/28922 | 5/2000 |
| 2006/0079956 A1 | 4/2006 | Eigler et al. ........... 623/1.35 | WO | 00/44307 | 8/2000 |
| 2006/0173528 A1* | 8/2006 | Feld et al. .............. 623/1.15 | WO | 00/44309 | 8/2000 |
| 2007/0073376 A1 | 3/2007 | Krolik et al. ........... 623/1.11 | WO | 00/47134 | 8/2000 |
| 2007/0112418 A1* | 5/2007 | Eidenschink et al. ... 623/1.35 | WO | 00/48531 | 8/2000 |
| 2007/0135903 A1* | 6/2007 | Gregorich et al. ....... 623/1.35 | WO | 00/49951 | 8/2000 |
| | | | WO | 00/51523 | 9/2000 |
| | FOREIGN PATENT DOCUMENTS | | WO | 00/57813 | 10/2000 |
| DE | 9014845 | 2/1991 | WO | 00/67673 | 11/2000 |
| DE | 29701758 | 3/1997 | WO | 00/71054 | 11/2000 |
| DE | 29701883 | 5/1997 | WO | 00/71055 | 11/2000 |
| EP | 0479730 | 10/1991 | WO | 00/74595 | 12/2000 |
| EP | 0751752 | 1/1997 | WO | 01/21095 | 3/2001 |
| EP | 0783873 | 7/1997 | WO | 01/21109 | 3/2001 |
| EP | 0804907 | 11/1997 | WO | 01/21244 | 3/2001 |
| EP | 0479557 | 7/1998 | WO | 01/35715 | 5/2001 |
| EP | 0876805 | 11/1998 | WO | 01/35863 | 5/2001 |
| EP | 0880949 | 12/1998 | WO | 01/39697 | 6/2001 |
| EP | 0891751 | 1/1999 | WO | 01/39699 | 6/2001 |
| EP | 0895759 | 2/1999 | WO | 01/41677 | 6/2001 |
| EP | 0904745 | 3/1999 | WO | 01/43665 | 6/2001 |
| EP | 0937442 | 8/1999 | WO | 01/43809 | 6/2001 |
| EP | 0347023 | 12/1999 | WO | 01/45594 | 6/2001 |
| EP | 1031328 | 8/2000 | WO | 01/45785 | 6/2001 |
| EP | 1031329 | 8/2000 | WO | 01/49342 | 7/2001 |
| EP | 0883384 | 12/2000 | WO | 01/54621 | 8/2001 |
| EP | 0862392 | 8/2001 | WO | 01/54622 | 8/2001 |
| EP | 0808140 | 12/2001 | WO | 01/58385 | 8/2001 |
| EP | 0884028 | 2/2002 | WO | 01/60284 | 8/2001 |
| | | | WO | 01/70294 | 9/2001 |

| | | |
|---|---|---|
| WO | 01/70299 | 9/2001 |
| WO | 01/74273 | 10/2001 |
| WO | 01/89409 | 11/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2006/028925 | 3/2006 |

OTHER PUBLICATIONS

U.S. Appl. No. 09/614,472, filed Jul. 11, 2000, Davidson et al.

U.S. Appl. No. 09/663,111, filed Sep. 15, 2000, Davidson et al.

Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).

Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).

Caputo, Ronald P., "Stent Jail: A Minimum-Security Prison," *The American Journal of Cardiology*, vol. 77, pp. 1226-1230 (Jun. 1, 1996).

Colombo, M.D., Antonio, ""Kissing" Stent for Bifurcational Coronary Lesion," *Catheterization and Cardiovascular Diagnosis*, vol. 30, pp. 327-330 (Dec. 1993).

Carrie, M.D., Didier, ""T"-Shaped Stent Placement: A Technique for the Treatment of Dissected Bifurcation Lesions," *Catheterization and Cardiovascular Diagnosis*, vol. 37, pp. 311-313 (Mar. 1996).

Katoh, M.D., Osamu, "New Double Wire Technique to Stent Ostial Lesions," *Catheterization and Cardiovascular Diagnosis*, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).

Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).

Satler, M.D., Lowell F., "Bifurcation Disease: To Treat or Not to Treat," *Catheterization and Cardiovascular Interventions*, vol. 50, pp. 411-412 (2000).

\* cited by examiner

BIFURCATED STENT

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments, this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. §1.72. The abstract is not intended to be used for interpreting the scope of the claims.

BRIEF SUMMARY OF THE INVENTION

The invention contemplates a new apparatus that simplifies placement of a stent at the bifurcation of a vessel. The invention creates an asymmetric region within the side branch petal region of the bifurcation stent. The asymmetric region is designed to lessen withdrawal forces created by balloon and catheter friction and snags on the proximal side of the petal region.

At least one of the embodiments of the present invention includes a medical device with a balloon catheter shaft, such as described in U.S. Pat. No. 6,835,203, the entire contents of which being incorporated herein by reference.

In at least one embodiment the stent comprises a substantially tubular body comprised of a plurality of interconnected struts and defining a circumferential plane. The tubular body has a proximal end region, a distal end region, and defines a first lumen therethrough, the first lumen having a first longitudinal axis. The tubular body comprises a plurality of adjacent deployable elements (or "petals") positioned between the proximal end region and distal end region. In an expanded configuration, the deployable elements define a second lumen which has a second longitudinal axis. The second longitudinal axis is at an oblique angle relative to the first longitudinal axis and the first lumen is in fluid communication with the second lumen. The substantially tubular body further comprises a track region comprising at least two struts which are substantially parallel to each other and the first longitudinal axis in the unexpanded configuration. The track region comprises at least one of the deployable elements.

In at least one embodiment, the tubular branch body further comprises a plurality of connectors. The track region has at least one connector engaged to at least one of the adjacent deployable elements. In another advantageous embodiment, at least one of these connectors is substantially curvilinear.

In at least one embodiment the track region further comprises at least one connector engaged between the at least two struts. In some embodiments at least one of these connectors is substantially curvilinear.

In some embodiments, the track region further comprises a plurality of connectors such that the adjacent deployable elements are engaged to each other by at least one connector. In at least one embodiment, the plurality of connectors define a substantially planar circumferential region about the second longitudinal axis.

In an advantageous embodiment, the stent comprises a substantially tubular body defining a circumferential plane. The tubular body has a proximal end region, a distal end region, and defines a first lumen therethrough, the first lumen having a first longitudinal axis. The tubular body comprises a plurality of adjacent deployable elements. In an expanded configuration the deployable elements define a second lumen which has a second longitudinal axis. The second longitudinal axis is at an oblique angle relative to the first longitudinal axis, and the first lumen is in fluid communication with the second lumen. Each deployable element consists of at least one curved stent member, the adjacent curved stent members defining a plurality of cells. In an expanded configuration each cell extends at an oblique angle relative to the second longitudinal axis. In at least one embodiment, the second lumen defines a substantially frusto-conical region when the stent is in an expanded configuration.

In another embodiment, the frusto-conical region has a first end region, a second end region, and a middle region therebetween. The first end region is defined by base cells, the second end region is defined by top cells, and the middle region is defined by middle cells. Each base cell has a greater area than each middle cell, and each middle cell has a greater area than each peak cell.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE DRAWINGS

A detailed description of the invention is hereafter described with specific reference being made to the drawings.

DETAILED DESCRIPTION OF THE INVENTION

Figure 1:
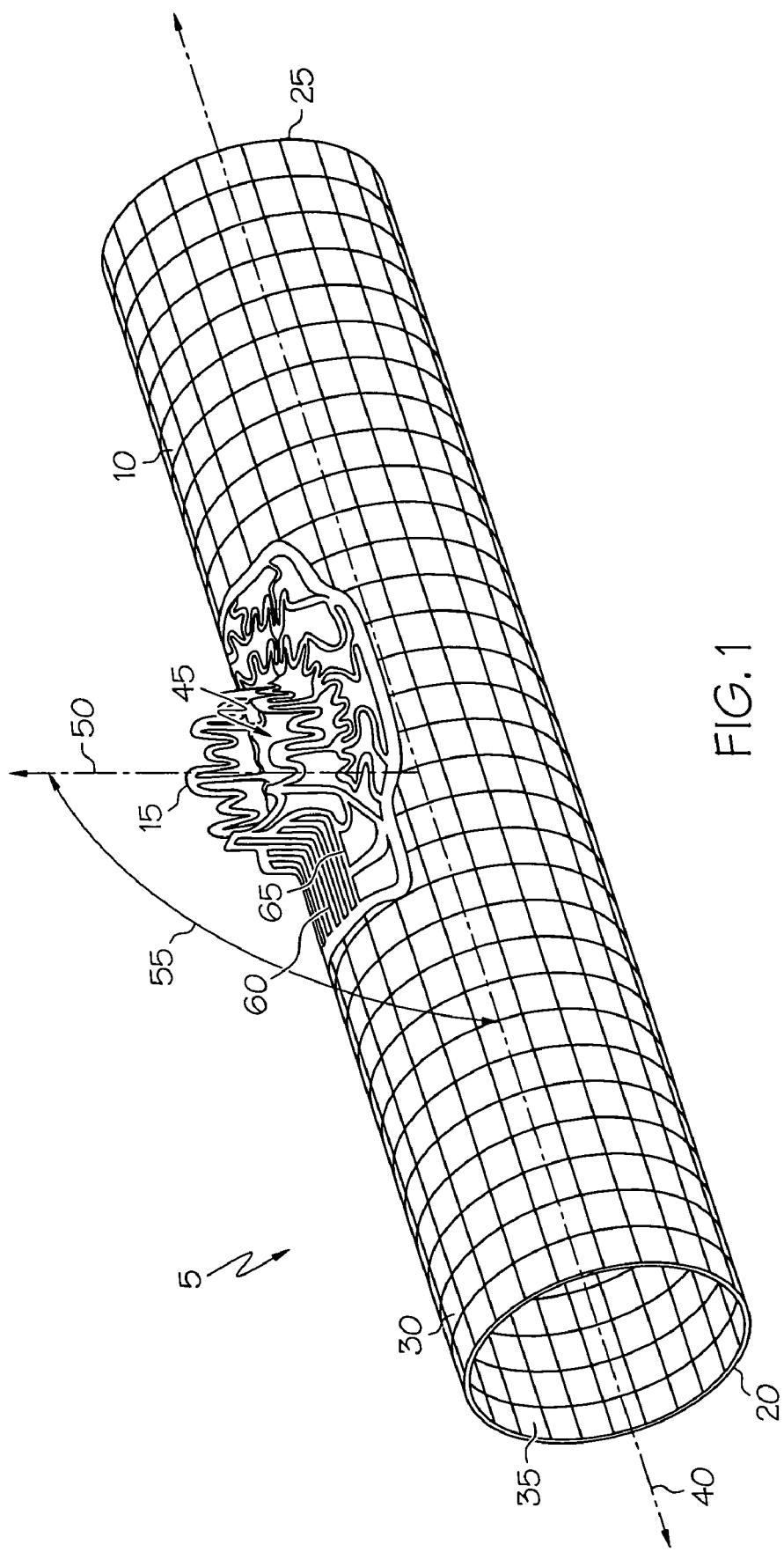
FIG. 1 is a side perspective view of an embodiment of the invention, in an expanded configuration, comprising a track region with substantially parallel struts.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Depicted in the figures are various aspects of the invention. Elements depicted in one figure may be combined with, and/or substituted for, elements depicted in another figure as desired.

Referring now to the drawings, which are intended to illustrate embodiments of the invention only and not for the purpose of limiting same, in at least one embodiment of the invention, an example of which is shown in FIG. 1, a bifurcated stent, shown generally at 5, comprises a substantially tubular body 10 defining a circumferential plane with deployable elements 15. The embodiment shown in FIG. 1 is in the expanded configuration. The tubular body 10, having a proximal end region 20 and a distal end region 25, is comprised of a plurality of interconnected struts 30. Proximal end region 20 and distal end region 25 define a first lumen 35 therethrough. First lumen 35 has a first longitudinal axis 40. Deployable elements 15 are positioned between proximal end region 20 and distal end region 25. In the expanded configuration, deployable elements 15 (or "petals) define a second lumen 45, extending along a second longitudinal axis 50. The region comprising deployable elements 15 is hereafter referred to as the petal region. The second longitudinal axis 50 is at an oblique angle 55 relative to the first longitudinal axis 40. Furthermore, the first lumen 35 is in fluid communication with the second lumen 45.

Figure 2:
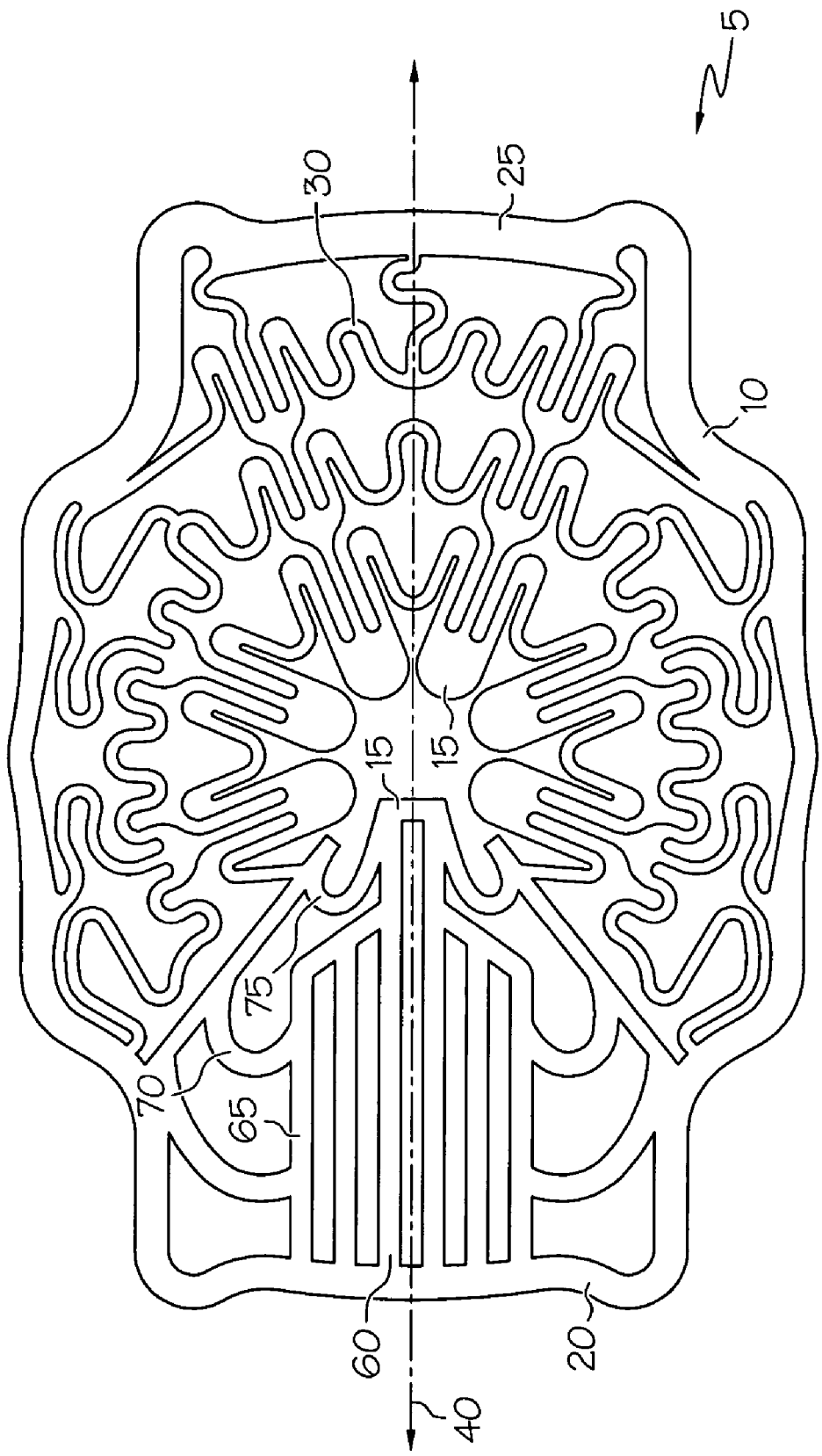
FIG. 2 is a top view of an embodiment of the invention, in an unexpanded configuration, comprising a track region with substantially parallel struts.
Figure 4:
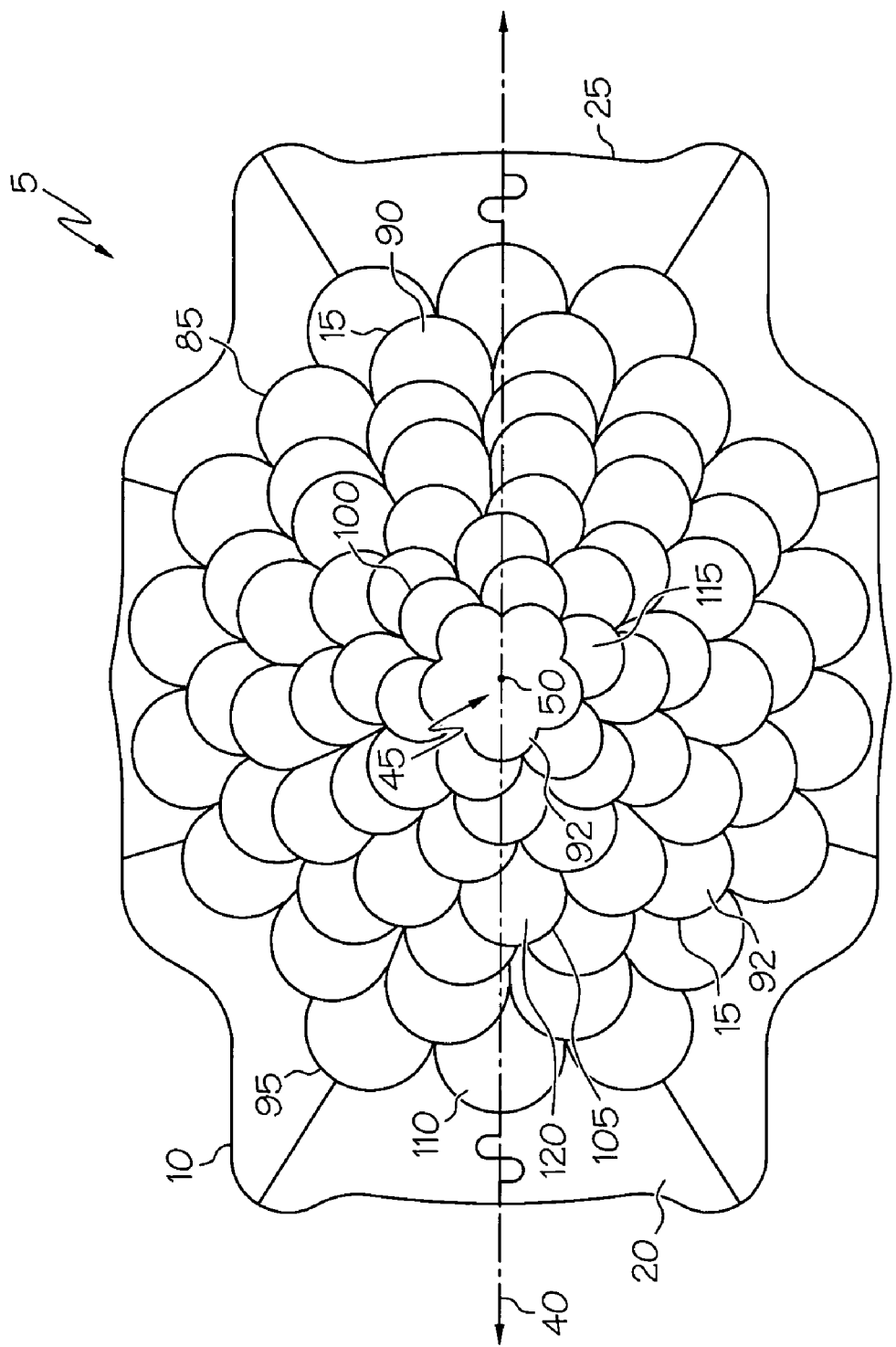
FIG. 4 is a top view of an embodiment of the invention, in an expanded configuration, comprising stent members that define base, middle, and top cells.

The tubular body 10, with proximal end region 20 and distal end region 25, further includes a track region 60 comprised of at least two parallel struts 65, shown in greater detail in FIGS. 2 and 4. Current stent designs include many points which may snag balloons on removal. Also, current stent designs include connecting struts which are often perpendicular to withdrawal forces, creating friction during withdrawal or even damaging drug coatings. In the invention, because the parallel struts 65 are substantially parallel to the first longitudinal axis 40 and aligned with the direction of the withdrawal force, the parallel struts 65 may lower the amount of friction caused during stent removal in comparison with stent designs with struts aligned across the direction of force. In at least one embodiment, the track region 60 is located at the proximal end region 20 of the tubular body 10. Locating the track region 60 at the proximal end region 20 of the tubular body 10 may further reduce the amount of friction caused during stent removal because the track region is located closest to where force is applied. The track region 60 comprises at least one of the deployable elements 15. In some embodiments, all areas of the petal region where the balloon might rub during withdrawal include a track region designed similarly in order to reduce friction during withdrawal.

FIG. 2 depicts stent 5, with deployable elements 15, extending along longitudinal axis 40. Unlike stent 5 of FIG. 1, stent 5 of FIG. 2 is shown in an unexpanded configuration. In the unexpanded configuration, deployable elements 15 do not extend to define a second lumen. Rather, the deployable elements 15 further substantially define the circumferential plane defined by tubular body 10. The tubular body 10, with proximal end region 20 and distal end region 25, further includes a track region 60 comprised of at least two parallel struts 65. The parallel struts 65, which are substantially parallel to the first longitudinal axis 40, may lower the amount of friction caused during stent removal. The track region 60 comprises at least one of the deployable elements 15.

In at least one embodiment, the tubular body 10 further includes a plurality of connectors 70. The track region 60 comprises at least one connector 70 engaged to at least one of the adjacent deployable elements 15. In some embodiments, at least one of the connectors 70 is substantially curvilinear. In an alternative embodiment, the track region also includes connectors 75 engaged between at least two parallel struts. In some embodiments, the connectors 75 are substantially curvilinear.

In some embodiments the stent may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto. A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

Figure 3:
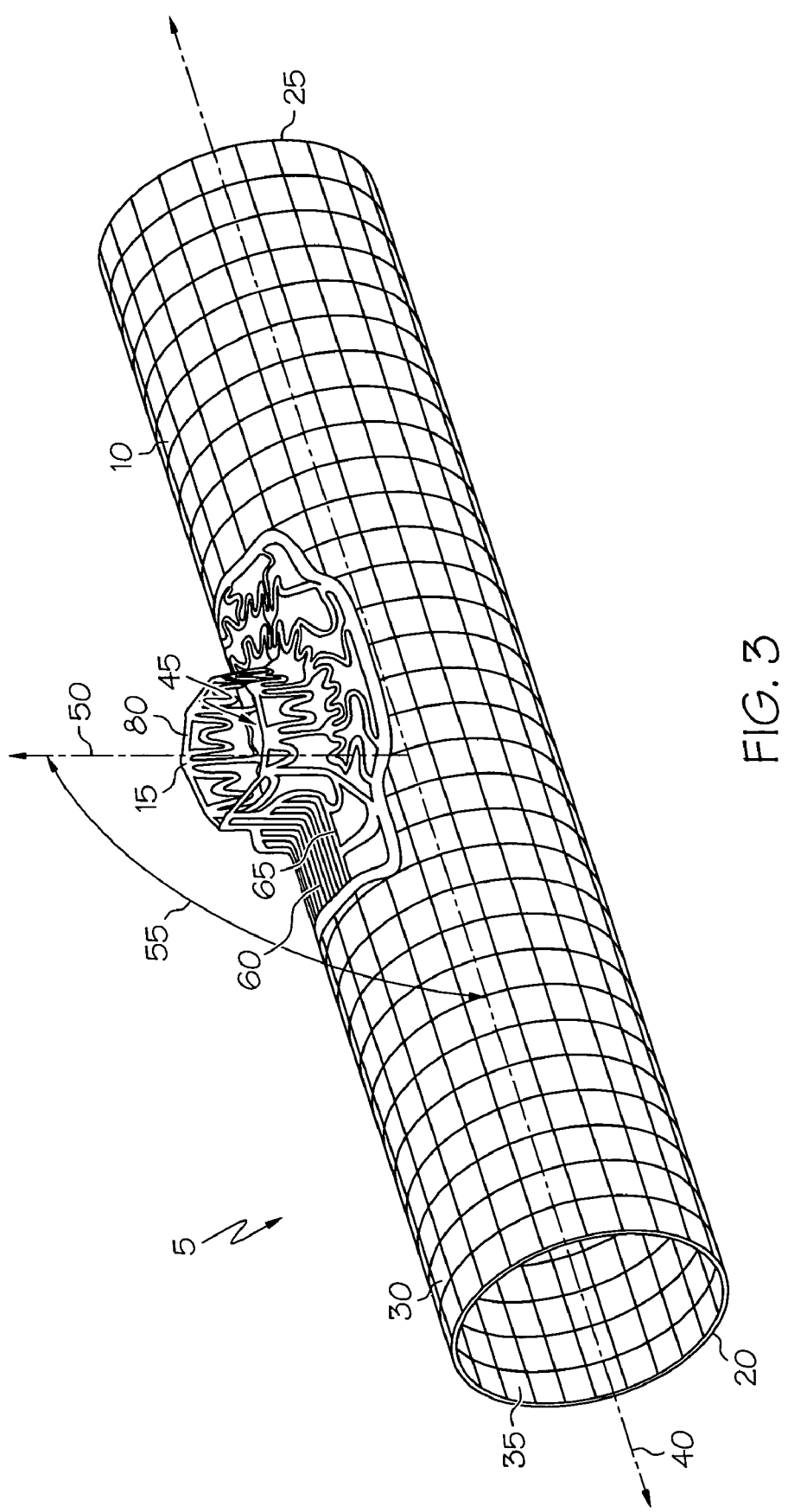
FIG. 3 is a side perspective view of an embodiment of the invention, in an expanded configuration, comprising a track region with substantially parallel struts and deployable elements joined together by connectors.

FIG. 3 shows stent 5 in an expanded configuration, extending along first longitudinal axis 40. Stent 5 comprises a substantially tubular body 10 with deployable elements 15. The tubular body 10, having a proximal end region 20 and a distal end region 25, defines a first lumen 35 therethrough. Furthermore, tubular body 10 is comprised of a plurality of interconnected struts 30. First lumen 35 has a first longitudinal axis 40. Deployable elements 15 are positioned between proximal end region 20 and distal end region 25. In the expanded configuration, deployable elements 15 define a second lumen 45, extending along a second longitudinal axis 50. The second longitudinal axis 50 is at an oblique angle 55 relative to the first longitudinal axis 40. Furthermore, the first lumen 35 is in fluid communication with the second lumen 45.

FIG. 3 further includes track region 60 which is desirably placed on the proximal side of the petal region. In one embodiment, adjacent deployable elements 15 are joined to each other by at least one connector 80. By using connectors 80, the deployable elements will, in the expanded configuration, present a smoothly undulating, or preferably straight, crown rather than one with discernible peaks. In at least one embodiment, a plurality of connectors 80 forms an annular, substantially planar, region about second longitudinal axis 50.

Figure 5:
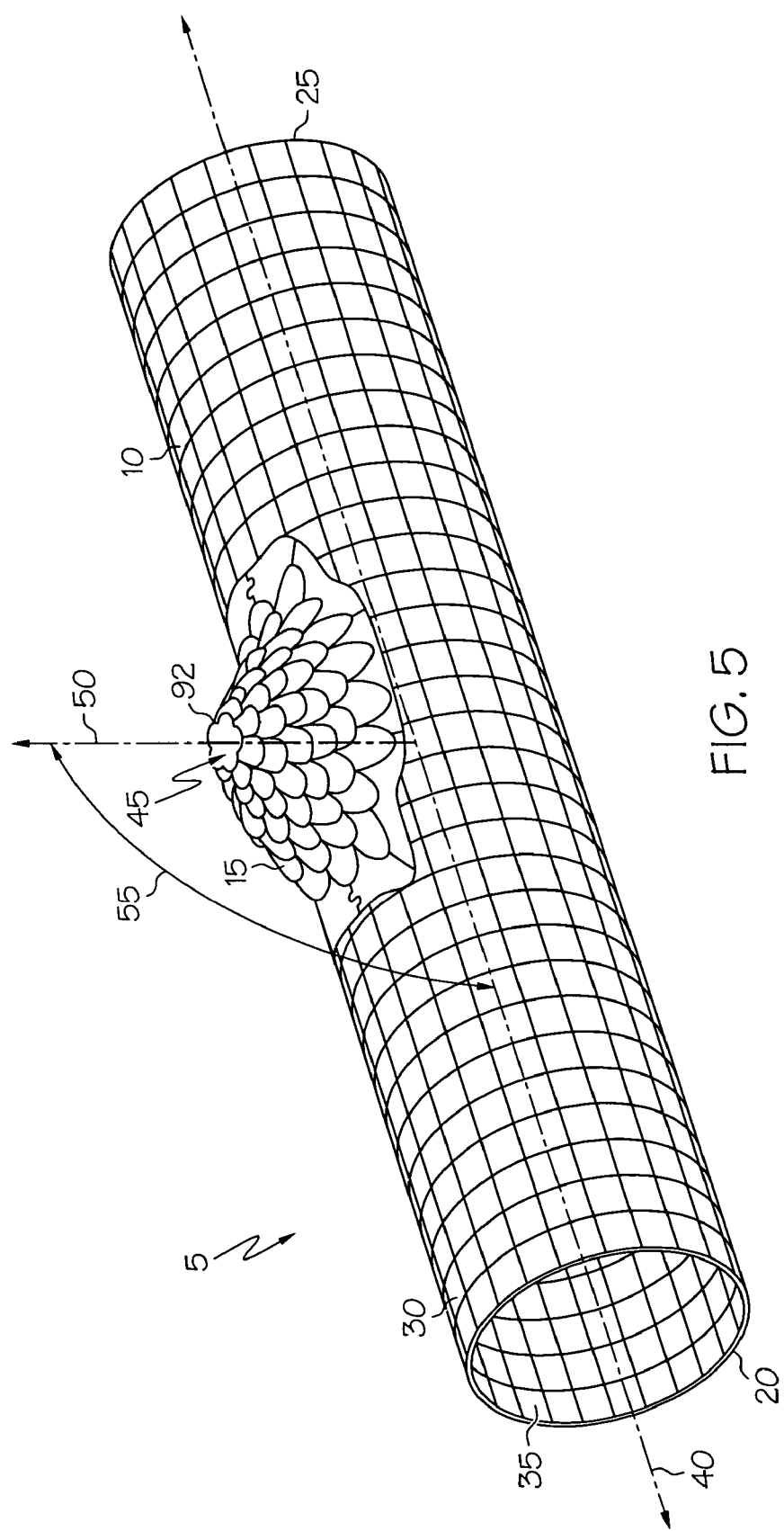
FIG. 5 is a side perspective view of the embodiment shown in FIG. 4, in an expanded configuration, comprising stent members that define base, middle, and top cells

In FIGS. 4 and 5, stent 5 is shown in an expanded configuration. Stent 5 is comprised of a substantially tubular body 10 with proximal end region 20 and distal end region 25. Tubular body 10, comprised of interconnected struts 30 (as shown in FIG. 5), defines a first lumen 35, which extends along first longitudinal axis 40, and comprises a plurality of adjacent deployable elements 15. Deployable elements 15 define a second lumen 45 which extends along second longitudinal axis 50. The second longitudinal axis 50 is at an oblique angle 55 relative to the first longitudinal axis 40, as seen in FIG. 5. Second lumen 45 is in fluid communication with first lumen 35.

As shown in FIG. 4, each deployable element consists of one curved stent member 85. Adjacent stent members 85 define a plurality of cells 90. In the expanded configuration, in at least one embodiment, the second lumen 45 defines a substantial frusto-conical region 92, as shown in FIG. 4. The frusto-conical region has a first end region 95, a second end region 100, and a middle region 105 therebetween. First end region 95 is defined by base cells 110, middle region 105 is defined by middle cells 120, and second end region 100 is defined by top cells 115. Each base cell 110 has a greater area than each middle cell 120, and each middle cell 120 has a greater area than each top cell 115.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A stent for placement at a vessel bifurcation, the stent having an expanded configuration and an unexpanded configuration, the stent comprising:
    a substantially tubular body comprised of a plurality of interconnected struts defining a sidewall, the tubular body having a proximal end region, a distal end region, and defining a first lumen therethrough, the first lumen having a first longitudinal axis, the tubular body comprising a side branch structure and a support ring positioned between the proximal end region and distal end region said support ring surrounding said side branch structure, said side branch structure comprising a plurality of adjacent deployable elements, said deployable elements surrounding a side branch opening, in the expanded configuration the deployable elements defining a second lumen, the second lumen having a branch axis, the branch axis being at an angle relative to the first longitudinal axis, the first lumen being in fluid communication with the second lumen;
    the substantially tubular body comprising a track region located proximal to the side branch opening, the track region comprising at least two struts which are straight and parallel to each other and the first longitudinal axis in the unexpanded configuration, each of said at least two struts defining at least a portion of at least one of the deployable elements at one end and attached to said support ring at another end, each of the at least two struts comprised of a first portion and a second portion, the first portion and second portion defining a portion of the first lumen in the unexpanded configuration,
    wherein in the expanded configuration, the first portion of the at least two struts defines a portion of the first lumen, and the second portion of the at least two struts defines a portion of the second lumen.

2. The stent of claim 1 wherein the tubular body further comprises a plurality of connectors, the track region having at least one connector, the at least one connector engaged to at least one of the adjacent deployable elements.

3. The stent of claim 2 wherein the at least one connector is substantially curvilinear.

4. The stent of claim 1 wherein the track region further comprises at least one connector engaged between the at least two struts.

5. The stent of claim 4 wherein the at least one connector is substantially curvilinear.

6. The stent of claim 1 wherein the track region further comprises a plurality of connectors, the adjacent deployable elements being engaged to each other by at least one connector.

7. The stent of claim 6 wherein the plurality of connectors define a circumferential region about the branch axis.

8. The stent of claim 1, wherein the plurality of adjacent deployable elements form peaks, the peaks being joined by a plurality of connectors, the peaks of adjacent deployable elements being joined to one another by at least one connector.

9. The stent of claim 8, wherein the plurality of connectors form an annular region about the branch axis.

10. The stent of claim 1, wherein said at least two struts of the track region are circumferentially adjacent to one another.

11. A stent comprising:
a tubular body comprising a plurality of interconnected structural members, the structural members defining a main branch structure, a side branch structure and a support ring extending continuously around the side branch structure the tubular body defining a longitudinal axis;

the side branch structure comprising a side branch ring defining a side branch opening, the side branch ring comprising a plurality of deployable elements, the side branch structure further comprising a track region, the track region comprising a plurality of track struts, the track struts being straight and parallel to one another and parallel to the longitudinal axis, each track strut attached at one end to the side branch ring and attached at the other end to the support ring; wherein in an expanded configuration, a first portion of each track strut defines a portion of a main branch lumen, and a second portion of each track strut defines a portion of a side branch lumen, the side branch lumen oriented nonparallel to the main branch lumen.

12. The stent of claim 11, wherein the track struts are oriented parallel to a central axis of the tubular body.

13. The stent of claim 11, wherein the track region further comprises a plurality of guide struts, each guide strut being straight and oriented parallel to the track struts.

14. The stent of claim 13, wherein each guide strut is attached at one end to the support ring.

15. The stent of claim 11, wherein the track struts are circumferentially adjacent to one another.

* * * * *